United States Patent [19]

Smith

[11] Patent Number: 5,181,915
[45] Date of Patent: Jan. 26, 1993

[54] REUSABLE DIAPER

[76] Inventor: Marshall D. Smith, P.O. Box 11, Atmora, Ala. 36504

[21] Appl. No.: 436,591

[22] Filed: Nov. 15, 1989

[51] Int. Cl.⁵ .................. A61F 13/15; A61F 13/20
[52] U.S. Cl. .................. 604/385.1; 604/358; 604/386; 604/391; 604/393; 604/402
[58] Field of Search .......... 604/385.1, 383, 385.1, 604/386, 391, 393, 398, 402, 358, 379–380, 397

[56] References Cited

U.S. PATENT DOCUMENTS

| | | | |
|---|---|---|---|
| 1,003,487 | 9/1911 | Miller-Jones | 604/358 |
| 2,660,172 | 11/1953 | Tittle | 604/386 |
| 3,029,816 | 4/1962 | Neils | 604/385.1 |
| 3,559,648 | 2/1971 | Mason, Jr. | 604/375 |
| 3,731,689 | 5/1973 | Schaar | 604/385.1 |
| 3,955,575 | 5/1976 | Okuda | 604/391 |
| 4,216,773 | 8/1980 | Ryan | 604/385.1 |
| 4,850,987 | 7/1989 | Gilomen | 604/385.1 |

*Primary Examiner*—Randall L. Green
*Assistant Examiner*—Paul Zuttarelli
*Attorney, Agent, or Firm*—Gregory M. Friedlander & Associates

[57] ABSTRACT

A reusable cloth diaper made more easily fitted by being stretchable without requiring the use of non-cloth materials by providing a pattern of folding to allow the diaper to stretch at an angle to the straight of the fabric or on the bias of the fabric with a minimum of stitching, having directions printed thereon for the use thereof.

5 Claims, 1 Drawing Sheet

REUSABLE DIAPER

BACKGROUND OF THE INVENTION

Prior Art

The invention relates to diapers.

More particularly, the invention relates to diapers which stretch to fit.

U.S. Pat. No. 3,081,772 shows an absorbent pre-fabricated diaper. It shows the use of Velcro TM attachments. U.S. Pat. No. 3,110,312 shows a diaper with a padded seat having an absorbent layer and having a similar type of attachment, being shaped around the legs of the child.

U.S. Pat. No. 3,359,980 also shows the use of Velcro TM fasteners in an adjustable and reusable diaper.

U.S. Pat. No. 3,955,575 shows the use of layering with Velcro TM fastening-type structure and also shows the use of folds in order to prevent spillage, although the exact methods those folds are provided for are somewhat different from that provided for in this invention.

U.S. Pat. No. 4,681,581 presents several different designs, including designs providing for bunching around the child's legs and various methods of using belts and Velcro TM for the purpose of fastening the diaper and discloses a Velcro TM fastening of the same type used in the preferred embodiment.

U.S. Pat. No. 4,704,117 mainly deals with the method of construction of an artificial non-cloth type diaper, but does utilize Velcro TM and does have means for providing sealing function around the legs of a child.

U.S. Pat. No. 4,773,906 provides a method for allowing air drying, again using Velcro TM and utilizes the use of elastic strips in order to have a snug fit around the waist and legs of the user. It is important that this is a reusable type of diaper, with means for allowing quick drying by unfolding to some extent.

U.S. Pat. No. 4,801,298 is also a reusable type, variable size diaper utilizing Velcro TM.

It also mainly deals with the method of manufacturing, the specific aspects of this and utilizes multiple patterns put together in order to form a single unit.

U.S. Pat. No. 4,826,498 uses an absorbent sheet in a diaper.

The use of Velcro TM in these patents is made without reference to the stretch characteristics of the fabrics.

U.S. Pat. No. 3,141,461 shows a reusable breechcloth. It is adjustable in order to allow it to fit different sized persons and certain folds are provided for that purpose.

U.S. Pat. No. 4,402,690 shows one method of using elastic strips around the legs in order to hug the legs of an infant in order to prevent spillage. It uses quilt stitches for moisture distribution purposes.

U.S. Pat. No. 4,775,375 shows the usage of bunching in order to prevent spillage and is otherwise unremarkable in terms of this patent. Again, it should be noted that this is mainly related to the particular design of the folds utilized to make this particular patent.

Each of the listed patents discloses elements of the instant invention. None of them utilize the pattern disclosed in the invention described herein. Also, none of the disclosure utilized the inherent bias in a cloth diaper.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein.

GENERAL DISCUSSION OF THE INVENTION

The method of folding used in the invention is unique in that it is adjusted to utilize the stretchable bias inherent in square cloth fabric and has a minimum number of folds in order to take advantage of stretching tendencies of natural fiber.

Disposable diapers are creating a major problem in the diaper industry by accounting for tremendous amounts of the country's total waste. The present invention is designed in part to alleviate this by providing an alternative to disposable diapers which stretches to fit and is blodegradable.

The benefits of the new diaper include that it is less expensive than disposables because it uses only a single material, natural square cut cloth. Also, it is washable and reusable. It is also less expensive to wash than use a diaper service. Because it is made of cloth without synthetic stretchable fibers, it is safely machine washable and dryable.

Like much of the prior art, it uses no pins, and instead uses Velcro TM fasteners so that it is faster and safer to close. Because the device uses Velcro TM fasteners, it can be used by young children and arthritis victims.

The diaper disclosed is less expensive to make and more environmentally sound because it is made of blodegradable cloth and does not contain synthetic stretchable materials. Because it is bias-cut and stretchable, the diaper fits snugly and will not fall down. It also contains adjustable padding for additional absorbency when necessary.

The diaper is compact for ease in handling, storing, and pre-rinsing in a clean-flushed toilet.

Because the diapers themselves are reusable, there is no accumulation of dirty diapers, as occurs with disposables and with a diaper service.

As the device uses an all-cloth diaper, the possibility of an allergic reaction is also lessened. Because the diaper is all cloth, repair is easily accomplished.

It is therefore a purpose of this patent is to provide a diaper which is stretchable along the waist of the diaper having a minimum number of folds.

The purpose of the product generated is not only to provide for a disposable diaper substitute, but also to provide a cloth diaper which is easier to use, less expensive to manufacture, and more easily understandable to persons who have never used a reusable diaper. To this end, the diaper comes with instructions.

Another purpose is to provide a diaper which can be opened and washed for purposes of being easily cleaned.

It is another purpose of this invention to provide a diaper which does not utilize materials which will become damaged upon repeated washing or which are synthetic stretching materials.

DETAILED DISCUSSION OF THE PREFERRED EMBODIMENT(S)

Figure 1:
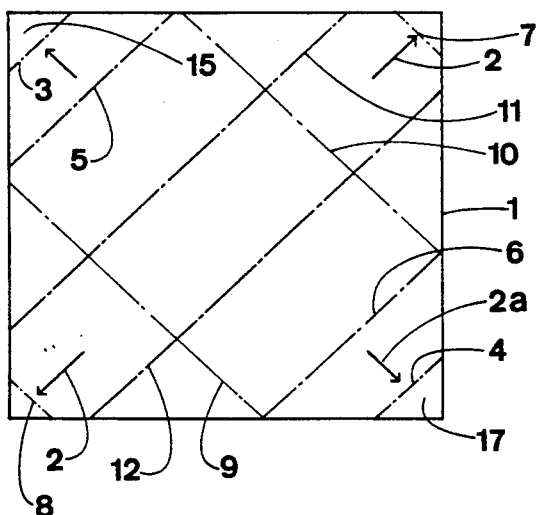
FIG. 1 shows a sheet of material used in manufacturing the diaper which is the subject of this invention with arrows indicating the bias of the fabric running at a 45° angle to the straight on threads of the diaper.

The description of the preferred embodiment is done in terms of a series of folds and stitches and defines both a product and a method for producing the product. Referring to FIG. 1, the folds are made in a sheet of material 1. The size of the material utilized in beginning the manufacture is largely determined by the size of the ultimate product. An example used in the preferred embodiment for making a relatively small diaper is to use a 27"×30" square of diaper material.

Because the diaper is designed to be opened completely, except at the stitching, the diaper uses manual folding about the wearer's legs by the individual using the diaper. In the preferred embodiment, instructions 35 and 36 are provided on the diaper for that folding.

Figure 4:
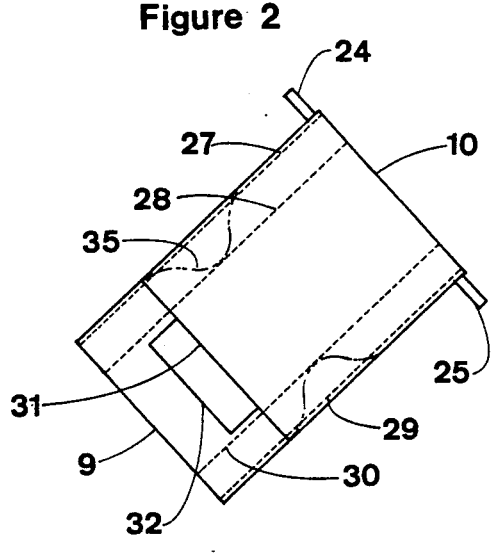
FIG. 4 shows the stitching and Velcro TM straps used in the diaper of FIG. 3.
Figure 5:
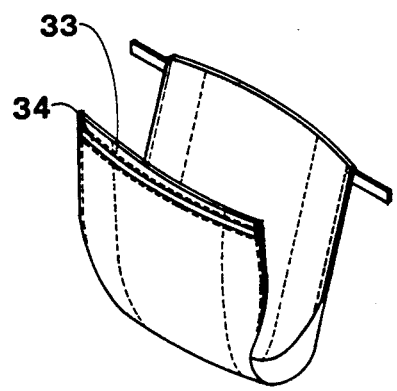
FIG. 5 shows the diaper after construction with the Velcro TM backing in place.
Figure 6:
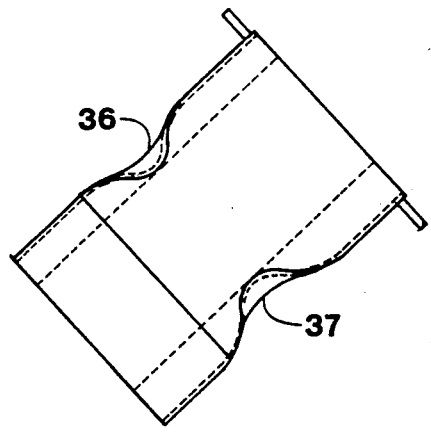
FIG. 6 shows an alternate view of the diaper shown in FIG. 5.

Prestitched folds, as opposed to manual folding, would make the device less sanitary because there would be cracks for the collection of soiling materials which would make cleaning more difficult. In the present invention, the diaper may be unfolded into a flat diaper as shown in FIG. 4. An alternative embodiment would allow for the replacement of all stitches with Velcro TM attachments so the diaper could be completely unfolded. This is not desired in the present invention because it would render the product unduly expensive.

Figure 2:
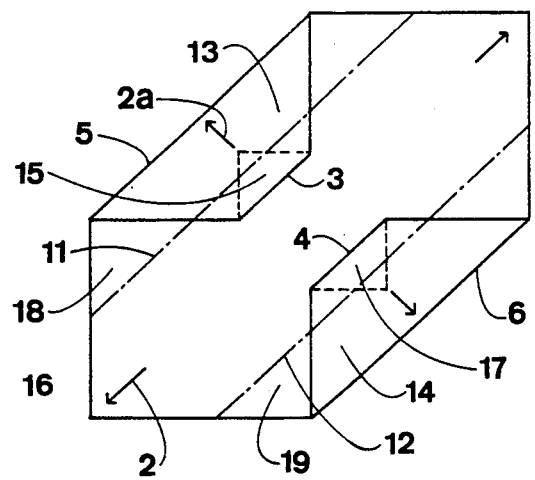
FIG. 2 shows the initial folds used in the cloth for purposes of manufacturing the diaper from FIG. 1.

The direction of stretch or bias 2 and 2a is shown in FIGS. 1 and 2. The bias 2 and 2a or stretch 2 and 2a of the material is a function given by the material having square air spaces inherent in square cut cloth. One bias is selected at random or the bias 2 and the other bias, perpendicular to the bias 2, is referred from the perpendicular bias 2a. There is some flexibility inherent in the threads of the fabric or the individual layers of fabric, because cloth fabric by nature is somewhat stretchable. A greater flexibility is derived from the combination of the flexibility of the threads and the air spaces formed by square weaving. This added flexibility is in the direction of the bias which is at a 45-degree angle to the straight of the fabric or the direction in which the threads run.

The bias 2 and perpendicular bias 2a versus the straight of the fabric is known in the art generally and is typically a problem when products are sewn along the straight as they tend to stretch out of shape when washed. This is not a problem in the present invention because the method of attachment, using Velcro TM allows for variable width as the material eventually becomes more stretched out. Also, the material wears out, requiring a new diaper at about the same time that the stretch-bias, perpendicular bias 2 and 2a, gives out for standard diaper material and the material tends to return on washing to the square cut based on the stitching which holds the cloth square as discussed below.

FIG. 1 shows the numbered folds which are used to form the diaper. The first folds are 3 and 4. The second folds are 5 and 6. The third folds are 11 and 12. The fourth folds are 7 and 8 and the fifth folds are 9 and 10. As is clear from the description below, all folds are parallel to the bias 2 or the perpendicular bias 2a of the material.

As can best be seen by reference to FIG. 2, the invention begins with folds 3 and 4 on opposing corners 15 and 17 of material 1. FIG. 1 shows the bias of the fabric using arrows 2. Since the bias 2 runs at a 45 degree angle from the direction of the threads, a second bias, the perpendicular bias 2a, runs from the center towards the corners 15 and 17.

As can be seen by reference to FIG. 2, folds 3 and 4 on either corner 15 and 17 of the material are made by taking the two corners 15 and 17 and folding them in towards the center along 16 the bias of the material. Next, folds 5 and 6 are made, further angling the opposite corners 15 and 17 towards the center 16.

Folds 5 and 6 are made, to outer wings 13 and 14. Following this, folds 11 and 12 are made to eliminate inner wings 18 and 19. At this point, the width of diaper is defined. Also, at this point, no stitching has been necessary. The bias 2a has been affected very little because no stitching affects bias 2a. Bias 2 has also been affected little, since the full length of the bias remains substantially the same.

A rectangular shape is desired for the preferred embodiment. In order to arrive at this shape, referring to FIG. 3, the diaper outer edges 20 and 21 are folded in along folds 7 and 8. Next the diaper ends 22 and 23 are folded along folds 9 and 10 onto center 6 to form a more or less rectangular block of material or a square diaper.

Figure 3:
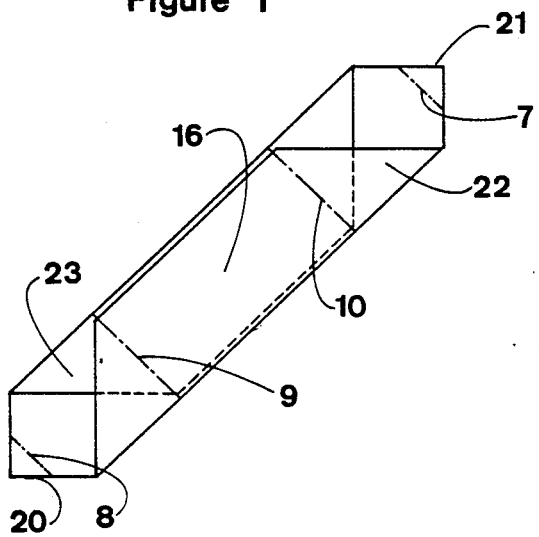
FIG. 3 shows the second set of folds used in manufacturing the diaper from FIG. 2.

Because of the unique method of folding, no stitching is required up to this point in time, and the rectangular block generated which is shown in FIG. 3 is stretchable along the bias 2 and perpendicular bias 2a of the material. At this point in time, prior to the stitching, the male ends of the Velcro TM 24 are inserted on either edge of the rectangular member as shown in FIG. 4 near the top of the said rectangular member so that a portion fits within the cloth rectangle between the upper layer and the lower layer formed by fold 5.

After folding as set forth above, the basic rectangular shape of the diaper, shown in FIG. 4, is accomplished. At this point in time, the diaper is ready for the initial stitching. Before beginning stitching, the fastening means, Velcro TM male strips 24 and 25 are inserted in the top end of the fabric. A space for the insertion of these strips 24 and 25 is formed by fold 10. The strips 24 and 25 are placed approximately one-half inch below the fold. Prior to stitching, the material is stretched in the direction of bias 2 and held stretched while the stitches 27, 28, 29 and 30 are made. These stitches not only hold the shape but may also serve to hold the velcro TM strips 24 and 25 in place.

Each end 22 and 23 are folded in toward the center section 31. Each of the ends 22 and 23 are only approximately 60 percent of the length of center section 6. Therefore, there is only a partial overlap of approximately 20 percent of the ends 22 and 23.

The partial overlap, as shown in FIG. 4, forms a pocket 31 after the material is stitched at 28 and 30. This pocket may be sealed with a stitch running from either end of pocket 31, but in the preferred embodiment, it is left open for inserting a pad 32 to comfort sitting and to add absorbency. As pad 32 is removable, it is easily washed or thrown away.

Stitches 27 and 29 are close to the edge and serve to hold Velcro TM inserts 24 and 25 as shown. Stitches 28 and 30 are closer to the center and serve to form the pocket 31 into which the additional absorbent pad 32 may be inserted as necessary.

The final stitching 33 adds a female Velcro ™ strip or backing 34 which is stitched one half inch below the top end of the rectangle opposite the male Velcro ™ which was previously applied. If a higher back or front was desired, the stitching of the strips could be changed to a higher or lower position from either end of the diaper as necessary. Prior to stitching the material as set forth above, the material is stretched in order to maintain as great an amount of the stretch associated with the bias as possible.

Directions 35 are provided at the bottom corners 36 and 37 showing the material to be folded in the places shown in order to prevent spillage. These directions are necessary as the average first-time consumer may be unaware of the technique for using the product. Manual folding for reasons cited above is preferred. The directions are dotted lines showing where the diaper is to be folded as it is applied.

In this case, a diaper approximately 9¼" wide and 15" long is generated. The folds for this type of diaper are usually 1½" in from the center.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

What is claimed:

1. A reusable cloth diaper manufactured from a square sheet of cloth material having two sets of two opposed corners, with a center section having a length therebetween, and comprised of a first and second set of threads woven together, said first set of threads running in a direction perpendicular to said second set of threads and having a straight corresponding to the direction the first set of threads run and wherein a first bias with two ends and is formed in a direction diagonal to the direction which the first set of threads run, said center section having four sides, and a perpendicular bias with two ends and at right angles to the first bias, so that at each end of the first bias and perpendicular bias of the material end in opposing corners, said diaper having:
   (a) the two opposed corners of one of said sets of opposed corners of the sheet folded towards the center section along the first bias of the material to form outer wings and the other two corners of the other set defining two diaper ends;
   (b) the two outer wings folded towards the center section along the first bias of the material to form two outer edges of the center section;
   (c) the two diaper ends folded towards the center section along the perpendicular bias to form two sides of the center section;
   (d) the outer edges folded along the perpendicular bias to form two perpendicular sides of the center section leaving a rectangle of cloth and further comprising;
   (e) at least one first stitch running parallel to the first bias, said at least one first stitch extending through the outer edges and folded ends to maintain their folded configuration.

2. The diaper of claim 1 wherein the rectangle of cloth has a top and bottom and a front side and a back side and further comprises;
   (f) a cooperating male and female hook and loop fastening means, said female loop fastening means being attached near the top on the front side of the rectangle of cloth and wherein;
   (g) there are two cooperating male hook fastening means attached to the perpendicular side of the rectangle of cloth so that the cooperating male hook fastening means and the female loop fastening means cooperate when the rectangle of cloth is folded.

3. The diaper of claim 1 wherein prior to stitching:
   (f) the rectangle of cloth is stretched in the direction of the first bias while the at least one first stitch is made.

4. The diaper of claim 1 wherein the diaper further comprises:
   (f) at least one of said diaper ends folded along the perpendicular bias to form a side of the center section leaving a rectangle of cloth and wherein the end that is folded is shorter than the length of the center section so that there is only a partial overlap of the ends;
   (g) a second stitch running parallel to the first stitch so that a pocket is formed between the first and second stitches near the center section of the rectangle of cloth after the material is stitched.

5. The diaper of claim 4 further comprising a pad which is removable and which is designed to fit within the pocket.

* * * * *